United States Patent [19]
Harpold et al.

[11] Patent Number: 5,369,028
[45] Date of Patent: Nov. 29, 1994

[54] DNA AND MRNA ENCODING HUMAN NEURONAL NICOTINIC ACETYLCHOLINE RECEPTOR COMPOSITIONS AND CELLS TRANSFORMED WITH SAME

[75] Inventors: Michael M. Harpold; Steven B. Ellis both of San Diego, Calif. Velicelebi, all of San Diego, Calif.

[73] Assignee: The Salk Institute Biotechnology/Industrial Associates, Inc., San Diego, Calif.

[21] Appl. No.: 504,455

[22] Filed: Apr. 3, 1990

[51] Int. Cl.⁵ .................. C12N 1/20; C12P 21/06; C12P 21/04; C07H 17/00
[52] U.S. Cl. .................. 435/252.3; 435/69.1; 435/69.7; 435/70.1; 435/71.1; 435/71.2; 536/23.5; 536/25.3
[58] Field of Search .................. 536/27, 23.5, 25.3; 435/69.1, 70.1, 240.1, 255, 91, 172.3, 252.3, 69.7, 71.1, 71.2

[56] References Cited

PUBLICATIONS

Marshall et al. *The EMBO Journal*, vol. 9, No. 13, pp. 4391–4398.
Deneris et al. *Neuron*, vol. 1, pp. 45–54, 1988.
Kurosaki, et al., "Functional properties of nicotinic acetylcholine receptor subunits expressed in various combinations," *FEBS Letters* 214, 253–258 (1987).
Wada, et al., "Functional expression of a new pharmacological subtype of brain nicotinic acetylcholine receptor," *Science*, 240:330–334 (1988).
Boulter, et al., "Isolation of a cDNA clone coding for a possible neural nicotinic acetylcholine receptor α-subunit," *Nature*, 319:368–374 (1986).
Boulter, et al., "Functional expression of two neuronal nicotinic acetylcholine receptors from cDNA clones identifies a gene family," *Proc. Natl. Acad. Sci.*, 84:7763–7767 (1987).
Goldman, et al., "Members of a nicotinic acetylcholine receptor gene family are expressd in different regions of the mammallian central nervous system," *Cell*, 48:965–973 (1987).
Patrick, et al., "Acetylcholine receptor metabolism in a nonfusing muscle cell line," *J. Biol. Chem.*, 25:2143–2153 (1977).
Dascal N., "The uses of xenopus oocytes for the study of ion channels," *CRC Crit. Rev. Biochem.*, 22:317–387 (1987).
Clementi, et al., "Pharmacological characterization of cholinergic receptors in a human neuroblastoma cell line," *J. Neurochem.*, 47:291–297 (1986).
Subramani, et al., "Expression of the mouse dihydrofolate reductase complementary deoxyribonucleic acid in simian virus 40," *Mol. Cell Biol.*, 1:854–864 (1981).
Deschamps, et al., "Identification of a transcriptional enhancer element upsteam from the proto-oncogene fos," *Science*, 230:1174–1177 (1985).

Primary Examiner—Margaret Parr
Assistant Examiner—Bradley L. Sisson
Attorney, Agent, or Firm—Pretty, Schroeder, Brueggemann & Clark

[57] ABSTRACT

Human neuronal nicotinic acetylcholine receptor subunits are described, as are methods for producing cells containing functional receptors employing such subunits. Also described are assay methods for determining the presence of functional HnAChRs in transfected cells, and for determining the agonist or antagonist activity of compounds with respect to such cells.

18 Claims, 14 Drawing Sheets

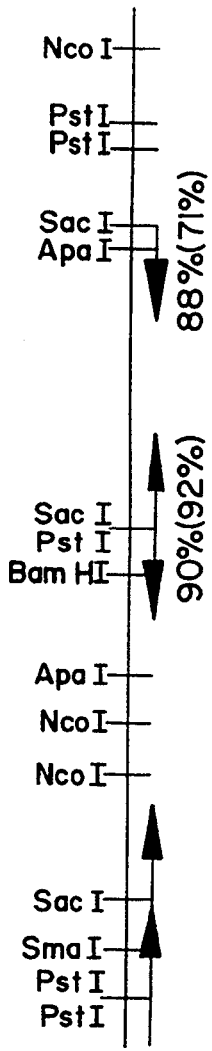
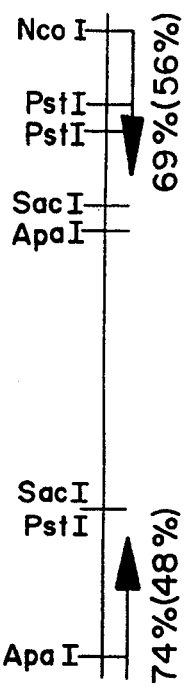
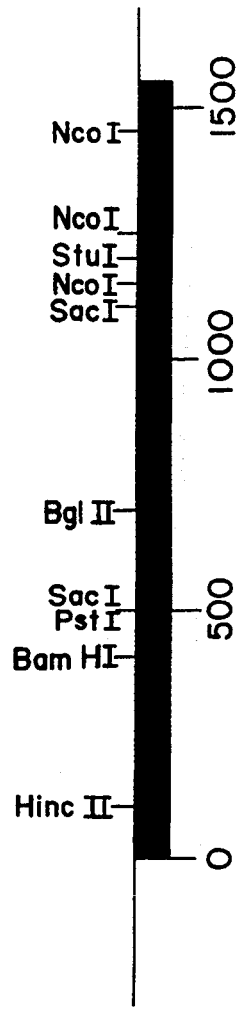
FIG. 4A Th 2.1 (2000 bp)
FIG. 4B Th. 2.11 (1300 bp)
FIG. 4C Th. 2.13 (1500 bp) / rat alpa 2

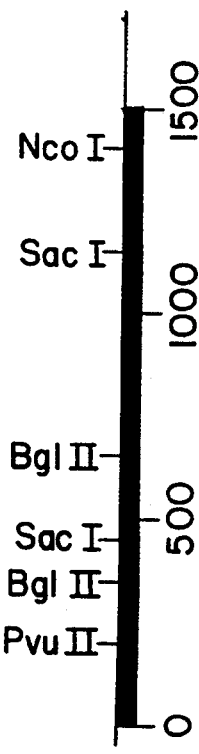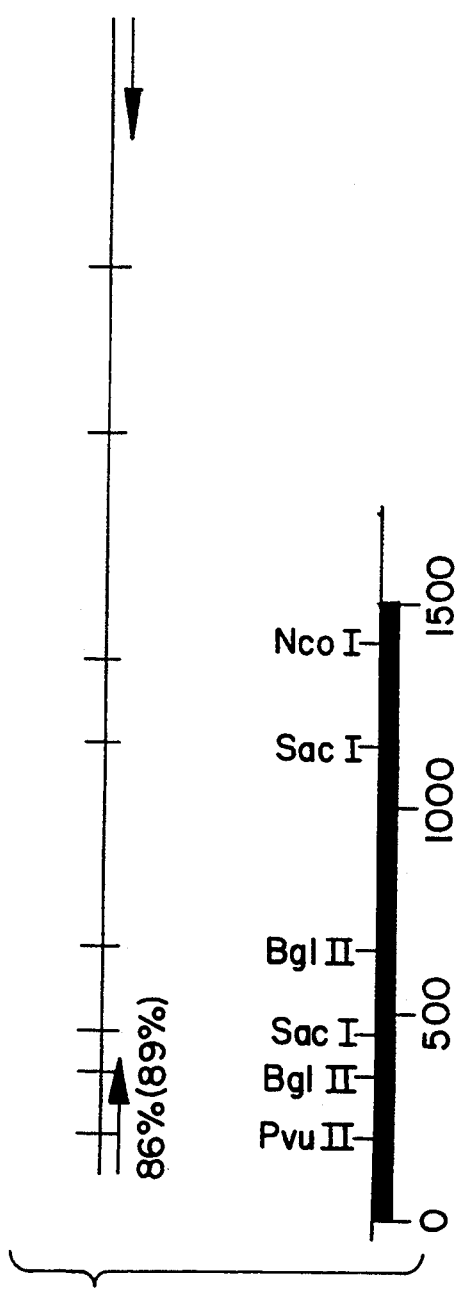
FIG. 5A B.S. 3.3 (2500 bp)
FIG. 5B B.S. 3.5 (2800 bp)
rat alpha 3

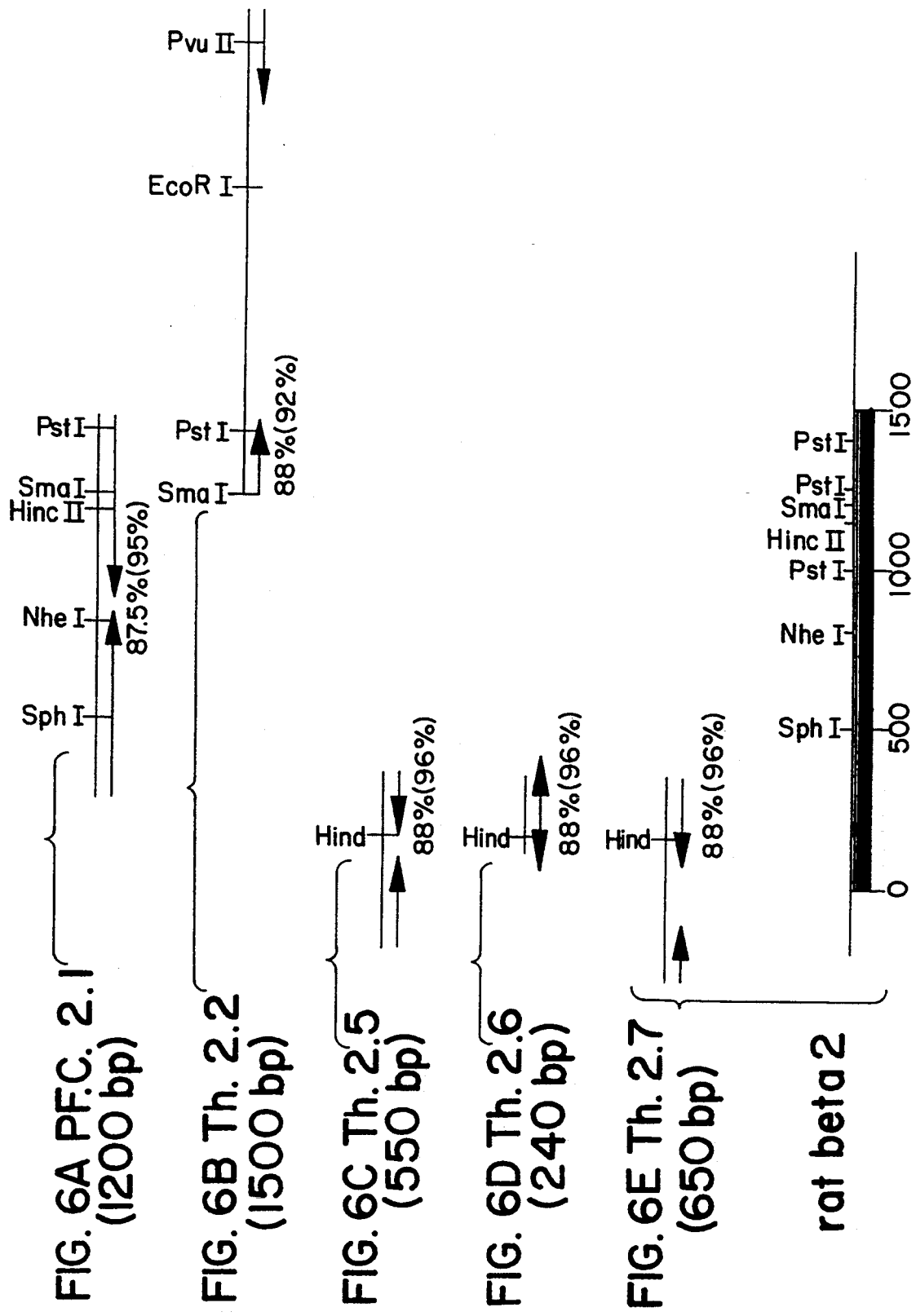

```
195 ...........GCTAAACAGGAGTGGAGCGACTACAAACTGCGCTGGAAC 157
            || |||||| ||||  |||||||||| |||||||||| ||
251 CCAATGTCTGGCTAAAGCAGGAATGGAATGACTACAAGCTGCGCTGGGAC 300

156 CCCGCTGATTTTGGCAACATCACATCTCTCAGGGTCCCTTCTGAGATGAT 107
    || |||||  |||||||| |||| || ||  | |||||||| ||||||||
301 CCGGCTGAGTTTGGCAATGTCACCTCCCTGCGCGTCCCTTCAGAGATGAT 350

BamHI
106 CT GGATCC CCGACATTGTTCTCTACAACAA...AAATGGGGAGTTTGCAG 60
    || |||||| |||||||| |||||||||||  | |||||||||||||| |
351 CT GGATCC AGACATTGTCCTCTACAACAATGCAGATGGGGAGTTTGCGG 400

59 TGACCCACATGACCAAGGCCCACCTCTTCTCCACGGGCACTGTGCACTGG 10
    |||||||||||||||||||| ||||||||| |||||||||||||||||||
401 TGACCCACATGACCAAGGCTCACCTCTTCTTCACGGGCACTGTGCACTGG 450

9 GTGCCCCCC
    |||||||||
451 GTGCCCCCA         FIG. 7A
```

```
  1 CCCCTTCGACCAGCAGAACTGCAAGATGAAGTTTGGCTCCTGGACTTATG 50
    |||||||||||||||||||||||||||||||||||||||||||| ||||
501 CCCCTTCGACCAGCAGAACTGCAAGATGAAGTTTGGCTCCTGGACATATG 550

51 ACAAGGCCAAGATCGACCTGGAGCAGATGGAGCAGACTGTGGACCTGAAG 100
    ||||||||||||||||| |||||||||||||||| ||| |||||||||||
551 ACAAGGCCAAGATCGATCTGGAGCAGATGGAGAGGACAGTGGACCTGAAG 600

101 GACTACTGGGAGAGCGGCGAGTGGGCCATCGTCAATGCCACGGGCACCTA 150
    ||||||||||||||| |||||||||||| | |||||||||| || ||||
601 GACTACTGGGAGAGTGGCGAGTGGGCCATTATCAATGCCACCGGAACCTA 650

151 CAACAGCAAGAAGTACGACTGCTGCGCCGAGATCTACCCCGACGTCACCT 200
    ||||| ||||||||||||||||||| |||||||||||||||| |||||||
651 TAACAGTAAGAAGTACGACTGCTGCGGAGATCTACCCCGATGTCACCT 700

201 AG...................................... 202
    |
701 ACTACTTTGTGATCCGGCGGCTGCCGCTGTTCTATACCATCAACCTCATC 750
```

FIG. 7B

```
  1 ....................CTGGCAGCAGAGGCTGAGCACCGTCTATTTG  31
                        || |||| |||||||||||| || ||
 51 GATGCTGCTGCCAGCGGCCAGTGCCTCAGAAGCTGAGCACCGCCTGTTCC 100

32 AGCGGCTGTTTGAAGATTACAATGAGATCATCCGGCCTGTAGCCAACGTG  81
    ||  ||||| ||||||||||||| |||||||||||||| || || || |||
101 AGTACCTGTTCGAAGATTACAACGAGATCATCCGGCCAGTGGCTAATGTG 150
                                          .PvuII
 82 TCTGACCCAGTCATCATCCATTTCGAGGTGTCCATGTCTCAGCTGGTGAA 131
    ||  | |||||||||||||| || |||||||||||||||||||||||||||
151 TCCCATCCAGTCATCATCCAGTTTGAGGTGTCCATGTCTCAGCTGGTGAA 200

132 GGTGGATGAAGTAAACCAGATCATGGAGACCAACCTGTGGCTCAAGCAAA 181
    |||||||||||||||||||||||||| |||||||||||||||| |||||||
201 GGTGGATGAAGTAAACCAGATCATGGAAACCAACCTGTGGCTGAAGCAAA 250

182 TCTGGAATGACTACAAGCTGAAGTGGAACCCCTCTGACTATGGTGGGCA  231
    ||||||||||||||||||||| ||||| |||||||||||    ||||
251 TCTGGAATGACTACAAGCTGAAATGGAAACCCTCTGACTACCAAGGGGTG 300
                             BglII
232 GAGTTCATGCGTGTCCCTGCACAGAAGATCTGGAAGCCAGACATTGT... 278
    |||||||||||||| |||||||||| ||||||||||| ||||||||| ||
301 GAGTTCATGCGTGTTCCTGCAGAGAAGATCTGGAAACCAGACATCGTACT 350
```

FIG. 8A

```
  1 ......................TTCCAGGTGGACGACAAGACCAAAGCCT  28
                          ||||||||||||| |||||||||||||||
351 GTACAACAACGCTGATGGGGATTTCCAGGTGGATGACAAGACCAAAGCTC 400

29 TACTCAAGTACACTGGGGACGTGACTTGGATACCTCCGGCCATCTTTAAG  78
    |||||||||||||  ||  ||||||||||||  |||||||||||||||||
401 TACTCAAGTACACAGGAGAAGTGACTTGGATCCCGCCGGCCATCTTTAAG 450
    SacI
 79 AGCTCCTGTAAAATCGACGTGACCTACTTCCCGTTTGATTACCAAAACTG 128
    |||||  || |||||||||||||||||||||||  ||  |||||||||||
451 AGCTCATGCAAAATCGACGTGACCTACTTCCCATTCGACTACCAAAACTG 500

129 TACCATGAAGTTCGGTTCCTGGTCCTACGATAAGGCGAAAATCGATCTGG 178
    ||||||||||||||| |||||||||||||| ||||  || ||||| ||||
501 CACCATGAAGTTCGGCTCCTGGTCCTACGACAAGGCAAAGATCGACCTGG 550

179 TCCTGATCGGCTCTTCCATGAACCTCAAGGACTATTGGGAGAGCGGCGAG 228
    ||||  |||||||| ||||||||||||||||||||  ||||||| |||||
551 TCCTCATCGGCTCCTCCATGAACCTCAAGGACTACTGGGAGAGTGGCGAG 600

229 TGGGCCATCATCAAAGCCCCAGGCTACAAACACGACATCAAGTACAACTG 278
    ||||| ||||| ||||||||| ||||||||||| ||| ||||||||||||
601 TGGGCTATCATTAAAGCCCCGGGCTACAAACATGAAATCAAGTACAACTG 650

279 CTGCGAGGAGATCTACCCCGACATCAC....'................. 305
    ||| ||||||||||||||  ||||||||
651 CTGTGAGGAGATCTACCAAGACATCACGTACTCGCTGTACATCCGTCGCC 700
```

FIG. 8B

```
  1 ATGCCCGCTGGCATGGCCCGGCGCTGCGGCCCCGTGGCGCTGCTCCTTGG  50
    ||||   |||  ||||||||  |||  ||  |   |    | ||||||||| ||      |
  1 ATGCTGGCTTGCATGGCCGGGCACTCCAACTCAATGGCGCTGTTC...AG  47

51 CTTCGGCCTCCTCCGGCTGTGCTCAGGGGTGTGGGGTACGGATACAGAGG 100
    ||||  ||||  ||   ||||||||||||||||  |  |||  ||  ||||||||
 48 CTTCAGCCTTCTTTGGCTGTGCTCAGGGGTTTTGGGAACTGACACAGAGG  97

101 AGCGGCTGGTGGAGCATCTCCTGGATCCTTCCCGCTACAACAAGCTTATC 150
    |||||||  ||||||||||||  ||||||  ||||||||  ||||||||| ||
 98 AGCGGCTAGTGGAGCATCTCTTAGATCCCTCCCGCTATAACAAGCTGATT 147

151 CGCCCAGCCACCAATGGCTCTGAGCTGGTGACAGTACAGCTTATGGTGTC 200
    ||  ||||||  ||  ||  ||||||||||||||||  ||||||||  |||||  ||
148 CGTCCAGCTACTAACGGCTCTGAGCTGGTGACTGTACAGCTCATGGTATC 197

201 ACTGGCCCAGCTCATCAGTGTGCATGAGCGGGAGCAGATCATGACCACCA 250
    |  ||||  |||||||||| ||||||  ||||||||||||||||||||||||||||||||
198 ATTGGCTCAGCTCATTAGTGTGCACGAGCGGGAGCAGATCATGACCACCA 247

251 ATGTCTGGCTGACCCAGGAGTGGGAAGATTATCGCCTCACCTGGAAGCCT 300
    ||||||||||||||||||||||||||||||||||||| ||||||||  |||||||||  ||||||||
248 ATGTCTGGCTGACCCAGGAGTGGGAAGATTACCGCCTCACATGGAAGCCT 297

301 GAAGAGTTTGACAACATGAAGAAAGTTCGGCTCCCTTCCAAACACATCTG 350
    ||  || ||  ||||||  |||||||||||||  ||||||||||||||||||||||||||||||
298 GAGGACTTCGACAATATGAAGAAAGTCCGGCTCCCTTCCAAACACATCTG 347
```

FIG. 9a-1

```
351 GCTCCCAGATGTGGTCCTGTACAACAATGCTGACGGCATGTACGAGGTGT 400
    |||||||||||||| || ||||||||||||||||||||||||| || |
348 GCTCCCAGATGTGGTTCTATACAACAATGCTGACGGCATGTACGAAGTCT 397

401 CCTTCTATTCCAATGCCGTGGTCTCCTATGATGGCAGCATCTTCTGGCTG 450
    ||||||||||||||| |||||||||||||||||||||| ||||| ||||
398 CCTTCTATTCCAATGCTGTGGTCTCCTATGATGGCAGGATCTTTTGGCTA 447

. SphI      .
451 CCGCCTGCCATCTACAAGAGCGCATGCAAGATTGAAGTAAAGCACTTCCC 500
    || |||||||||||||||||| |||||||||||| || ||||||||||
448 CCACCTGCCATCTACAAGAGTGCATGCAAGATTGAGGTGAAGCACTTCCC 497

501 ATTTGACCAGCAGAACTGCACCATGAAGTTCCGTTCGTGGACCTACGACC 550
    |||||||||||||| |||||||||||||||| || || ||||||||||
498 ATTTGACCAGCAGAATTGCACCATGAAGTTTCGCTCATGGACCTACGACC 547

551 GCACAGAGATCGACTTGGTGCTGAAGAGTGAGGTGGCCAGCCTGGACGAC 600
    | || ||||| ||| ||||||| || ||||| |||||||| ||||| |||
548 GTACTGAGATTGACCTGGTGCTCAAAAGTGATGTGGCCAGTCTGGATGAC 597

601 TTCACACCTAGTGGTGAGTGGGACATCGTGGCGCTGCCGGGCCGCGGCAA 650
    |||||||| || || |||||||||||| | || ||||| ||||    ||||
598 TTCACACCCAGCGGGGAGTGGGACATCATCGCACTGCCAGGCCGACGCAA 647

651 CGAGAACCCCGACGACTCTACGTACGTGGACATCACGTATGACTTCATCA 700
    ||||||||| ||||||||| || || |||||||||| |||||||||||||
648 CGAGAACCCAGACGACTCCACCTATGTGGACATCACCTATGACTTCATCA 697
```

FIG.9a-2

```
701  TTCGCCGCAAGCCGCTCTTCTACACCATCAACCTCATCATCCCCTGTGTG 750
     ||||  ||||| || ||||||||||| |||||||||||||||||||| ||
698  TTCGTCGCAAACCACTCTTCTACACTATCAACCTCATCATCCCCTGCGTA 747

751  CTCATCACCTCGCTAGCCATCCTTGTCTTCTACCTGCCATCCGACTGTGG 800
     ||||||||||||| |||||||| |||||||||||||| | |||||||||
748  CTCATCACCTCGCTGGCCATCCTGGTCTTCTACCTGCCCTCAGACTGTGG 797

801  CGAGAAGATGACGTTGTGCATCTCAGTGCTGCTGGCGCTCACGGTCTTCC 850
     ||  |||||||||| |||| | ||| || || |||||||||||| ||||
798  TGAAAAGATGACACTTTGTATTTCTGTGCTGCTAGCACTCACGGTGTTCC 847

851  TGCTGCTCATCTCCAAGATCGTGCCTCCCACCTCCCTCGACGTGCCGCTC 900
     |||||||||||||||||||| ||||||||||||||||||||| || |||
848  TGCTGCTCATCTCCAAGATTGTGCCTCCCACCTCCCTCGATGTACCGCTG 897

901  GTCGGCAAGTACCTCATGTTCACCATGGTGCTTGTCACCTTCTCCATCGT 950
     || ||||||||||||||||| ||||||||||||| |||||||||||||||
898  GTGGGCAAGTACCTCATGTTTACCATGGTGCTAGTCACCTTCTCCATCGT 947

951  CACCAGCGTGTGCGTGCTCAACGTGCACCACCGCTCGCCCACCACGCACA 1000
     |||||||||||| |||||||| |||||||||||||||||| |||||||||
948  CACCAGCGTGTGTGTGCTCAATGTGCACCACCGCTCGCCTACCACGCACA 997

1001 CCATGGCGCCCTGGGTGAAGGTCGTCTTCCTGGAGAAGCTGCCCGCGCTG 1050
     ||||||| |||||||||| ||| ||||||||||||||||||||| | |||
998  CCATGGCCCCCTGGGTCAAGGTGGTCTTCCTGGAGAAGCTGCCCACCCTG 1047
```

FIG. 9b-1

```
1051 CTCTTCATGCAGCAGCCACGCCATCATTGCGCCCGTCAGCGCCTGCGCCT 1100
     ||||||  ||||||||||||||||| | ||  || ||||||||  ||||| |
1048 CTCTTCCTGCAGCAGCCACGCCACCGCTGTGCACGTCAGCGTCTGCGCTT 1097

1101 GCGGCGACGCCAGCGTGAGCGCGAGGGCGCTGGAGCCCTCTTCTTCCGCG 1150
     | ||  ||||||||||  |||| ||||||   | ||  ||||||||||| |
1098 GAGGAGGCGCCAGCGAGAGCGTGAGGGC...GAGGCGGTTTTCTTCCGTG 1144

1151 AAGCCCCAGGGGCCGACTCCTGCACGTGCTTCGTCAACCGCGCGTCGGTG 1200
     |||  || | |||  ||| | ||  || ||||| ||||||| || || |||
1145 AAGGTCCTGCGGCTGACCCATGTACCTGCTTTGTCAACCCTGCATCAGTG 1194

1201 CAGGGGTTGGCCGGGGCCTTCGGGGCTGAGCCTGCACCAGTGGCGGGCCC 1250
     |||||  ||||| |||||  ||| |  |||||||||| |  ||  |||||
1195 CAGGGCTTGGCTGGGGCTTTCCGAGCTGAGCCCACTGCA...GCCGGCCC 1241

1251 CGGGCGCTCAGGGGAGCCGTGTGGCTGTGGCCTCCGGGAGGCGGTGGACG 1300
     ||||||||| | || |||  || |||||||||||||||||| || |||| |
1242 GGGGCGCTCTGTGGGCCATGCAGCTGTGGCCTCCGGGAAGCAGTGGATG 1291

1301 GCGTGCGCTTCATCGCAGACCACATGCGGAGCGAGGACGATGACCAGAGC 1350
     |||| ||||||||| || |||||||||||  || ||| ||||||||||||
1292 GCGTACGCTTCATTGCGGACCACATGCGAAGTGAGGATGATGACCAGAGT 1341

1351 GTGAGTGAGGACTGGAAGTACGTCGCCATGGTGATCGACCGCCTCTTCCT 1400
     ||||| ||||||||||| ||||| |||||||||||||||||||| ||||| 
1342 GTGAGGGAGGACTGGAAATACGTTGCCATGGTGATCGACCGCCTGTTCCT 1391
```

FIG.9b-2

```
                                                              PstI
1401 CTGGATCTTTGTCTTTGTCTGTGTCTTTGGCACCATCGGCATGTTCCTGC 1450
     |||||||||||||||||||||||||||| ||| |||||||||||||||
1392 GTGGATCTTTGTCTTTGTCTGTGTCTTTGGGACCGTCGGCATGTTCCTGC 1441

1451 AGCCTCTCTTCCAGAACTACACCACCACCACCTTCCTCCACTCAGACCAC 1500
     |||||||||||||||||||||||||| |||| ||||||||||| ||||||
1442 AGCCTCTCTTCCAGAACTACACTGCCACTACCTTCCTCCACCCTGACCAC 1491

1501 TCAGCCCCCAGCTCCAAGTGA 1521
     ||||| |||||||||||||||
1492 TCAGCTCCCAGCTCCAAGTGA 1512
```

FIG.9c

DNA AND MRNA ENCODING HUMAN NEURONAL NICOTINIC ACETYLCHOLINE RECEPTOR COMPOSITIONS AND CELLS TRANSFORMED WITH SAME

FIELD OF THE INVENTION

This invention relates to neuronal nicotinic acetylcholine receptor genes and proteins. In a particular aspect, the present invention relates to human neuronal nicotinic acetylcholine receptor genes and proteins. In a further aspect, the present invention relates to methods for determining the presence of neuronal nicotinic acetylcholine receptor activity in cells thought to have genes encoding such proteins. In yet another aspect, the present invention relates to methods for determining the agonist or antagonist activity of compounds which might interact with neuronal nicotinic acetylcholine receptors.

BACKGROUND OF THE INVENTION

Most theories on how the nervous system functions depend heavily on the existence and properties of cell to cell contacts known as synapses. For this reason, the study of synapses has been a focal point for neuroscience research for many decades.

Because of its accessibility to biochemical and electrophysiological techniques, and because of its elegant, well defined structure, the neuromuscular synapse (also known as the neuromuscular junction), which occurs at the point of nerve to muscle contact, is one of the most studied and best understood synapses. At the neuromuscular junction, the nerve cell releases a chemical neurotransmitter, acetylcholine, which binds to nicotinic acetylcholine receptor proteins located on post-synaptic muscle cells. The binding of acetylcholine results in a conformational change in the nicotinic acetylcholine receptor protein. This change is manifested by the opening of a transmembrane channel in the receptor which is permeable to cations. The resulting influx of cations depolarizes the muscle and ultimately leads to muscle contraction.

Biological and structural studies have shown that the nicotinic acetylcholine receptor in muscle is a glycoprotein composed of five subunits with the stoichiometry $\alpha\alpha\beta\delta\Delta$ (alpha-alpha-beta-gamma-delta). From these same studies, it is known that each of the subunits has a mass of about 50–60 kilodaltons and is encoded by a separate gene. In vitro reconstitution experiments have shown that this $\alpha\alpha\beta\delta\Delta$ complex is a functional receptor containing both ligand binding sites and a ligand-gated transmembrane channel.

It is now known that a variety of neurotransmitters and neurotransmitter receptors exist in the central and peripheral nervous systems. Despite this knowledge, there is still little understanding of the diversity of receptors for a particular neurotransmitter, or of how this diversity might generate different responses to a given neurotransmitter, or to other modulating ligands, in different regions of the brain. On a larger scale, there is little appreciation of how the use of a particular synapse makes it more or less efficient, or how long-term changes in neuronal circuits might be accomplished by the modification of synapses.

An understanding of the molecular mechanisms involved in neurotransmission in the central nervous system is limited by the complexity of the system. The cells are small, have extensive processes, and often have thousands of synapses deriving from inputs from many different parts of the brain. In addition, the actual number of neurotransmitter receptors is low, making their purification difficult, even under the best of circumstances. Consequently, neither cellular nor biochemical approaches to studying neurotransmission in the central nervous system has been particularly fruitful. This is unfortunate because it is quite probable that the treatment of dementia, Alzheimer's disease and other forms of mental illness will involve modification of synaptic transmission with specific drugs.

Nicotinic acetylcholine receptors found at the vertebrate neuromuscular junction, in vertebrate sympathetic ganglia and in the vertebrate central nervous system can be distinguished pharmacologically on the basis of ligands that open or block the ion channel. For example, the elapid $\alpha$-neurotoxins that block activation of nicotinic acetylcholine receptors at the neuromuscular junction do not block activation of neuronal nicotinic acetylcholine receptors found on several different cell lines.

To gain access to the neuronal acetylcholine receptors, traditional biochemical and neurophysiological methods have been abandoned in favor of the newer methods of molecular biology. More specifically, using molecular cloning techniques, complementary DNA clones were isolated which encode the acetylcholine receptor expressed in the Torpedo fish electric organ, a highly enriched source of receptor. The cDNA clones isolated from the fish electric organ were then used in nucleic acid hybridization experiments to obtain cDNA and genomic clones for the subunits of the acetylcholine receptor expressed in mouse skeletal muscle.

The availability of cDNA clones encoding muscle nicotinic receptors made it possible to extend these studies in the important direction of neuronal receptors. More specifically, based on the assumption that neuronal nicotinic receptors are evolutionarily related to muscle receptors, and that this relationship will be reflected at the genetic level by nucleotide sequence homology, the cDNA clones encoding the muscle nicotinic receptor were used to screen rat cDNA and genomic libraries for related neuronal mRNAs or genes. This method has resulted in the isolation of several neuronal cDNA clones that have significant sequence homology with the muscle acetylcholine clones.

That the neuronal nicotinic acetylcholine receptors differ from muscle nicotinic acetylcholine receptors is evidenced by the fact that neuronal receptors can be constituted from only two different gene products (i.e., one alpha subunit and one beta subunit). This is significant since, in all experiments reported to date, muscle nicotinic acetylcholine receptors have been formed with $\alpha\beta\delta\Delta$ subunits, $\alpha\beta\Delta$ subunits, $\alpha\beta\delta$ subunits or $\alpha\delta\Delta$ subunits, but not with any pairwise combinations. See Kurosaki et al., *FEBS Letters* 214, 253–258 (1987).

In order to further extend such studies, to provide proteins useful for assaying compounds as potential agonists or antagonists for human neuronal nicotinic acetylcholine receptors, as well as cell lines capable of expressing such proteins, we undertook to isolate and characterize clones which encode various subunits of the human neuronal nicotinic acetylcholine receptor; we further undertook to develop methods for expressing cloned human neuronal nicotinic acetylcholine receptor sequences in recombinant cell lines; and we further undertook to develop assays for identifying which of the resultant recombinant cell lines express functional neuronal nicotinic receptors.

SUMMARY OF THE INVENTION

In accordance with the present invention, we have isolated and characterized clones which encode the alpha2, alpha3 and beta2 subunits of the human neuronal nicotinic acetylcholine receptor.

The neuronal clones of the present invention encode a family of acetylcholine receptors having unique pharmacological properties. The demonstration that the nicotinic acetylcholine receptors are much more diverse than previously expected offers an opportunity for a high level of pharmaceutical intervention and a chance to design new drugs that affect specific receptor subunits. Such subtypes make it possible to observe the effect of a drug substance on a particular receptor subtype, which can be expressed in a recombinant cell in the absence of the other receptor subtypes. Information derived from these observations will allow the development of new drugs that are more specific, and therefore have fewer unwanted side effects.

In addition, the availability of human neuronal receptors makes it possible to perform initial in vitro screening of the drug substance in a test system which is specific for humans. While it is true that the drug eventually has to be administered directly to the human patient, it is probable that useful drugs are being missed because conventional drug screening is limited to assays employing non-human receptors, human tissue preparations (which are likely to be contaminated with other receptors, both nicotinic and non-nicotinic in origin), and other suboptimal assay systems. Consequently, the ability to screen drug substances in vitro on specific receptor subtype(s) is likely to be more informative than merely screening the drug substance employing presently available suboptimal assay systems.

Both the receptor subunit genes and proteins of the present invention can be used for drug design and screening. For example, the cDNA clones encoding the human alpha2, alpha3 and beta2 receptor subunits can be transcribed in vitro to produce mRNA. This mRNA, either from a single subunit clone or from a combination of clones, can then be injected into oocytes where the mRNA directs the synthesis of the human receptor molecule(s). The resulting receptor-expressing oocytes can then be contacted with a test compound, and the agonist or antagonist effect thereof can then be evaluated by comparing oocyte response relative to positive and negative control compounds and positive and negative control oocytes. Alternatively, the clones may be placed downstream from appropriate gene regulatory elements and inserted into the genome of eukaryotic cells. This will result in transformed cell lines expressing a specific human receptor subtype, or specific combinations of subtypes. The derived cell lines can then be produced in quantity for similar reproducible quantitative analysis of the effects of drugs on receptor function.

BRIEF DESCRIPTION OF THE FIGURES

The top panel of FIG. 1 is a restriction map of the alpha2 subunit gene of the human neuronal nicotinic acetylcholine receptor, compared to the corresponding rat gene (shown in the bottom panel of FIG. 1).

The top panel of FIG. 2 is a restriction map of the alpha3 subunit gene of the human neuronal nicotinic acetylcholine receptor, compared to the corresponding rat gene (shown in the bottom panel of FIG. 2).

Figure 3:
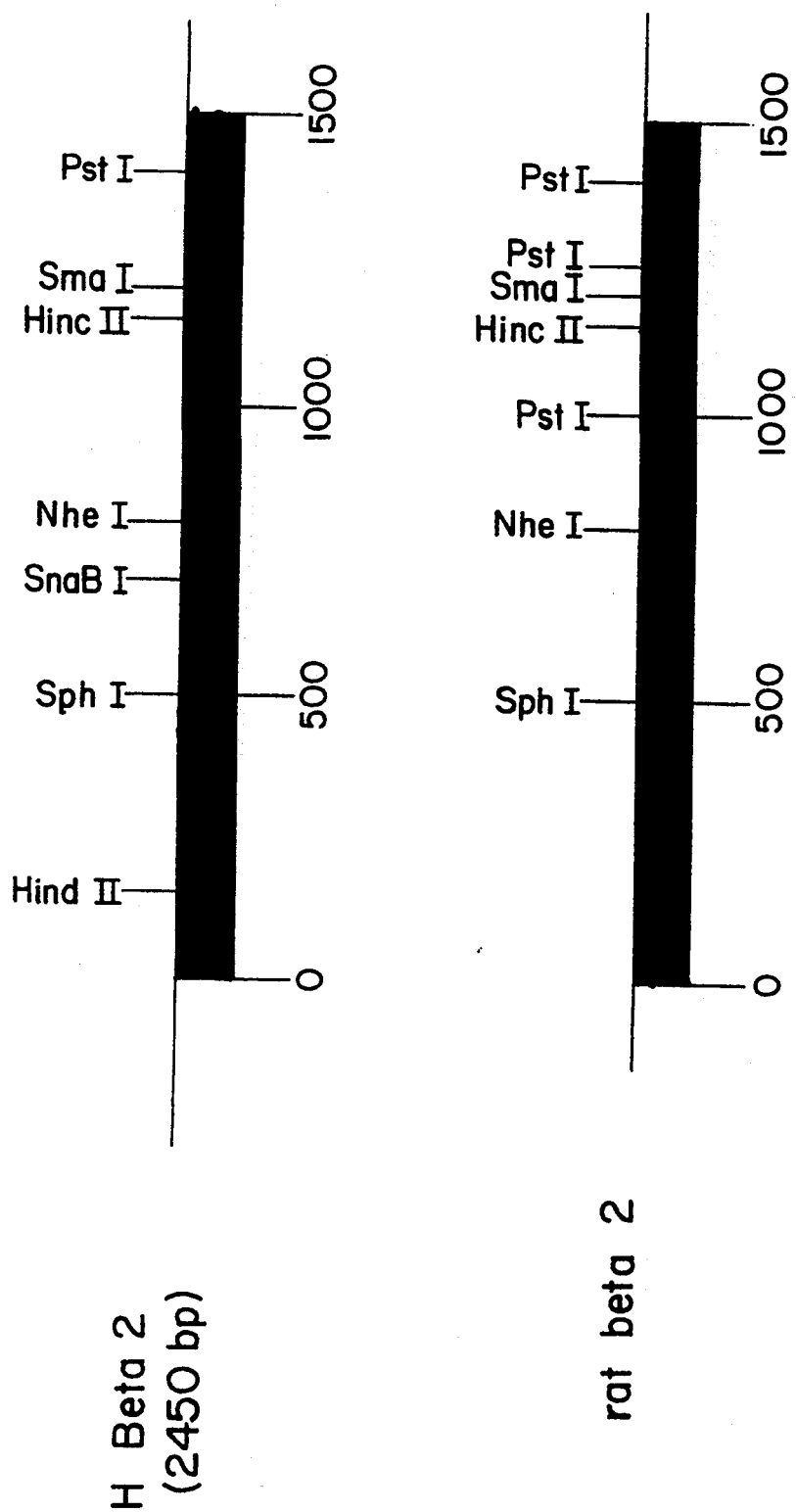

The top panel of FIG. 3 is a restriction map of the beta2 subunit gene of the human neuronal nicotinic acetylcholine receptor, compared to the rat gene (shown in the bottom panel of FIG 3).

FIG. 4 is a comparison of the alpha2 subunit gene of the rat neuronal nicotinic acetylcholine receptor (shown in the bottom panel of FIG. 4) with several cDNA fragments obtained from the human alpha2 subunit gene (i.e., fragment Th. 2.1, shown in panel A FIG. 4, and fragment Th. 2.11, shown in panel B of FIG. 4, and fragment Th. 2.13, shown in panel C of FIG. 4). The arrows beneath the various human cDNA fragments indicate the direction and extent of DNA sequencing carried out for the respective fragments.

FIG. 5 is a comparison of the alpha3 subunit gene of the rat neuronal nicotinic acetylcholine receptor (shown in the bottom panel of FIG. 5) with several cDNA fragments obtained from the human alpha3 subunit gene (i.e., fragment B.S. 3.3, shown in panel A of FIG. 5 and fragment B.S. 3.5, shown in panel B of FIG. 5). The arrows beneath the various human cDNA fragments indicate the direction and extent of DNA sequencing carried out for the respective fragments.

FIG. 6 is a comparison of the beta2 subunit gene of the rat neuronal nicotinic acetylcholine receptor (shown in the bottom panel of FIG. 6) with several cDNA fragments obtained from the human beta2 subunit gene (i.e., fragment PF.C. 2.1, shown in panel A of FIG. 6, fragment Th. 2.2, shown in panel B of FIG. 6, fragment Th. 2.5, shown in panel C of FIG. 6, fragment Th. 2.6, shown in panel D of FIG. 6, and fragment Th. 2.7, shown in panel E of FIG. 6). The arrows beneath the various human cDNA fragments indicate the direction and extent of DNA sequencing carried out for the respective fragments.

FIG. 7, Sections A and B, present a comparison of about 500 base pairs of human alpha2 sequence (presented in two portions, labeled as Section A and Section B, respectively with the corresponding rat sequence.

FIG. 8, Sections A and B, present a comparison of about 650 base pairs of human alpha3 sequence (presented in two portions, labeled a Section A and Section B, respectively) with the corresponding rat sequence.

FIG. 9, presented as sheets 9(a), 9(b), and 9(c), provides a comparison of the nucleotide sequence for the human and rat beta2 subunits.

DETAILED DESCRIPTION OF THE INVENTION

In accordance with the present invention, there are provided substantially pure DNA sequence(s) encoding alpha subunit(s) of the human neuronal nicotinic acetylcholine receptor and/or substantially pure DNA sequence(s) encoding beta subunit(s) of the human neuronal nicotinic acetylcholine receptor.

In accordance with a particular embodiment of the present invention, there are provided mRNA sequences and polypeptides encoded by the above-described DNA sequences.

In accordance with yet another embodiment of the present invention, there are provided cells transformed with one or more of the above-described DNA sequences.

In accordance with still another embodiment of the present invention, there are provided substantially pure human neuronal acetylcholine receptors comprising at least one human alpha receptor subunit and at least one human beta subunit.

In accordance with a further embodiment of the present invention, there are provided methods for measuring the agonist or antagonist activity of test compounds (with respect to human neuronal acetylcholine receptors or subunits thereof), by measuring the response of the above-described cells and/or receptors, relative to the response of a control, when contacted with said compound.

In accordance with the letter embodiment of the present invention, the response of the above-described cells and/or receptors is determined by such assays as:
nicotine binding,
$^{86}$Rb ion-flux,
the electrophysiological response of said cells, or
the electrophysiological response of oocytes transfected with RNA from said cells.

In accordance with yet another embodiment of the present invention, there is provided a method for assaying cells for the presence of neuronal nicotinic acetylcholine receptor activity. This is accomplished by determining the effect of known neuronal nicotinic acetylcholine agonists and/or antagonists on the influx of $^{86}$Rb ions into cells, relative to the rate of influx of $^{86}$Rb ions into control cells.

In accordance with a further embodiment of the present invention, there is provided an alternative method for assaying cells for the presence of neuronal nicotinic acetylcholine receptor activity, employing a multi-step screening protocol comprising the steps:
(a) analyzing those cells which are positive for the presence of alpha and beta subunit RNAs for their ability to bind nicotine or a nicotine agonists, relative to the nicotine binding ability of control cells known to express neuronal nicotinic acetylcholine receptors, and
(b) determining the effect of known neuronal nicotinic acetylcholine agonists and/or antagonists on cells having the ability to bind nicotine or nicotine agonist on the influx of $^{86}$Rb ions into said cells, relative to the rate of influx of $^{86}$Rb ions into control cells.

In accordance with a still further embodiment of the present invention, there is provided a method for making cells having neuronal nicotinic acetylcholine receptor activity, employing a multi-step protocol comprising the steps:
(a) transfecting host cells with DNA encoding at least one alpha subunit of the neuronal nicotinic acetylcholine receptor and at least one beta subunit of the neuronal nicotinic acetylcholine receptor, then
(b) analyzing said transfected cells for the presence of alpha and beta subunit RNAs, employing methods such as Northern blot or slot blot analysis, then
(c) analyzing those cells which are positive for the presence of alpha and beta subunit RNAs for their ability to bind nicotine or a nicotine agonist, relative to the nicotine binding ability of control cells known to express neuronal nicotinic acetylcholine receptors, and
(d) determining the effect of known neuronal nicotinic acetylcholine agonists and/or antagonists on cells having the ability to bind nicotine or a nicotine agonist on the influx of $^{86}$Rb ions into control cells.

In accordance with the preceding two embodiments of the present invention, mRNA from cells which are positive for alpha and beta neuronal nicotinic acetylcholine subunits is injected into oocytes, which are then assayed for the presence of functional neuronal nicotinic acetylcholine receptors.

As used herein, the term agonist refers to a substance that activates receptor function; and the term antagonist refers to a substance that interferes with receptor function. Antagonists are of two types: competitive and non-competitive. A competitive antagonist (or competitive blocker) competes with the neurotransmitter for the same binding site. A non-competitive antagonist or blocker inactivates the functioning of the receptor by binding to a site other than the acetylcholine binding site.

Figure 1:
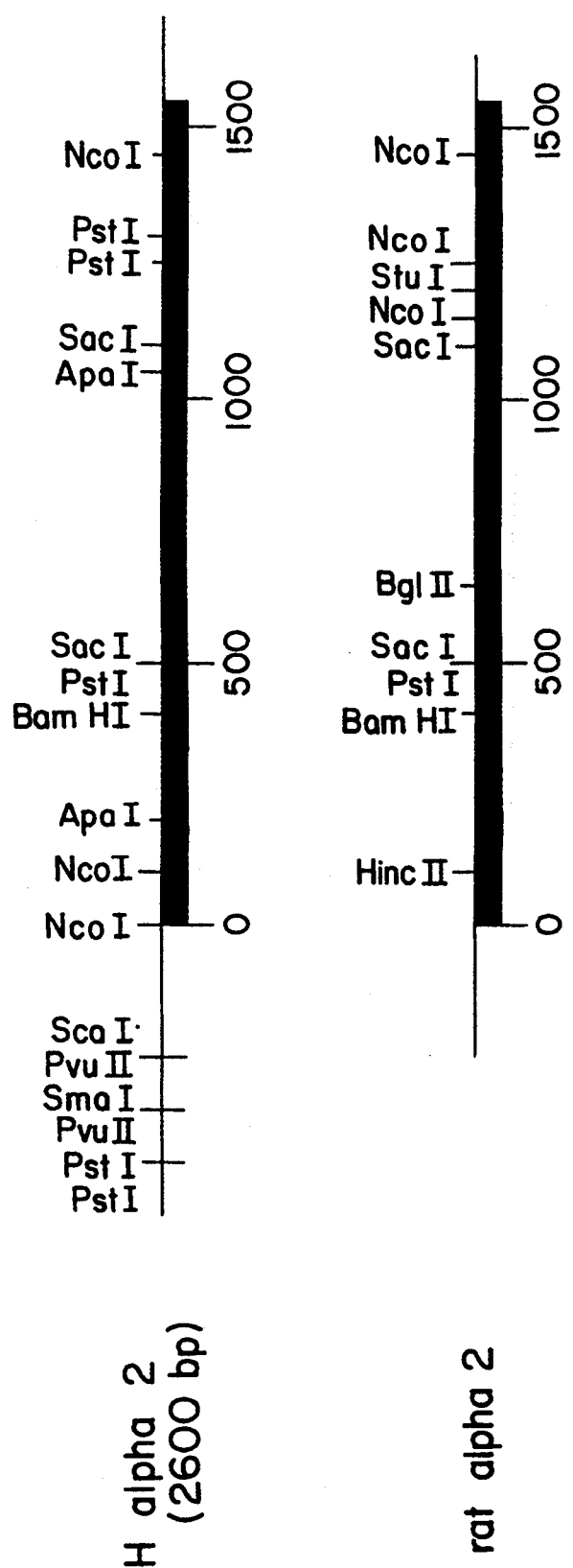

As used herein, alpha2 refers to a gene, which has been identified in chick and rat, that encodes a neuronal subunit of the same name. DNA coding for the human neuronal alpha2 subunit has been deposited with the ATCC; the DNA (designated as HnAChRα2; a restriction map of which is shown in FIG. 1; and a partial nucleotide sequence of which is shown in FIG. 7) has been accorded ATCC Accession No. 68277.

Figure 2:
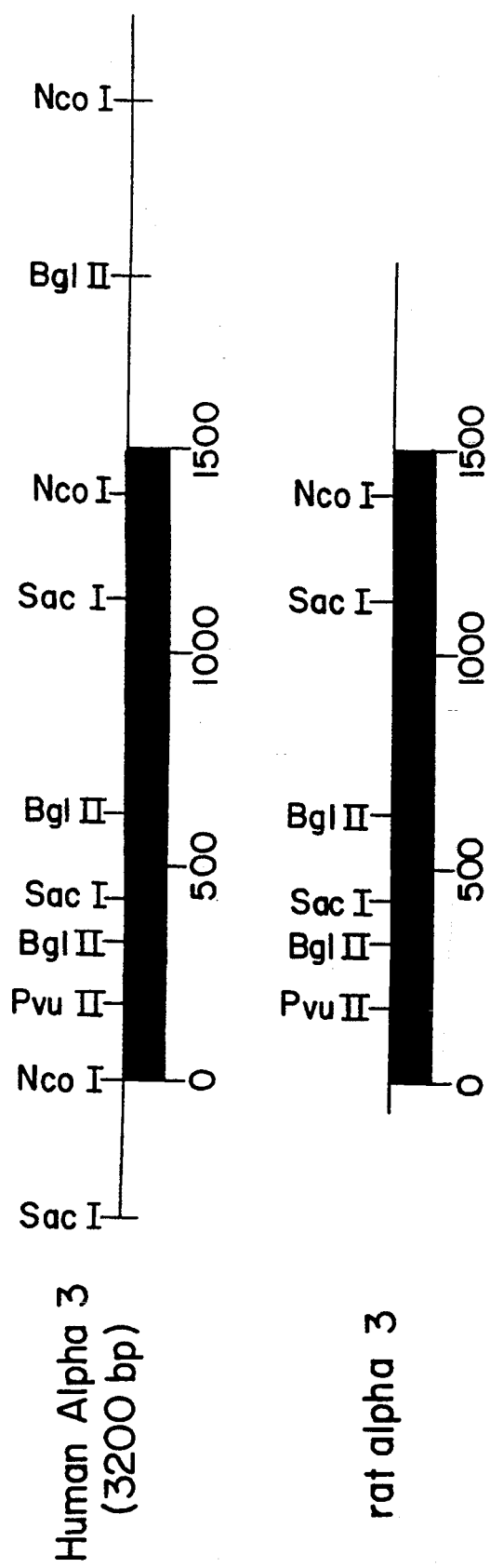

As used herein, alpha3 refers to a gene that encodes a neuronal subunit of the same name. DNA coding for the human alpha3 subunit has been deposited with the ATCC; the DNA (designated as HnAChRα3; a restriction map of which is shown in FIG. 2; and a partial nucleotide sequence of which is shown in FIG. 8) has been accorded ATCC Accession No. 68278.

As used herein, beta2 refers to a gene encoding a neuronal nicotinic acetylcholine subunit of the same name. DNA coding for the neuronal beta2 subunit has been deposited with the ATCC; the DNA (designated as HnAChRβ2; a restriction map of which is shown in FIG. 3; and the nucleotide sequence of which is shown in FIG. 9) has been accorded ATCC Accession No. 68279.

cDNA clones comprising human neuronal nicotinic acetylcholine receptor genes alpha2 (clone HnAChRα2), alpha3 (clone HnAChRα3), and beta2 (clone HnAChRβ2), all of which are in *E. coli* HB101, were deposited on Mar. 23, 1990, at the American Type Culture Collection, 12301 Parklawn Drive, Rockville, Md. 20852-1776, U.S.A. (ATCC) under the terms of the Budapest Treaty on the International Recognition of Deposits of Microorganisms for Purposes of Patent Procedure and the Regulations promulgated under this Treaty. Pursuant to the Budapest Treaty, the deposited strains will be maintained for a period of at least + years after the date of deposit, and for a period of at least five years after the most recent request for a sample. Samples of the cloned genes are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

Use of the phrase "substantial sequence homology" in the present specification and claims means that DNA, RNA or amino acid sequences which have slight and non-consequential sequence variations form the actual sequences disclosed and claimed herein are considered to be equivalent to the sequences of the present invention, and as such are within the scope of the appended claims. In this regard, "slight and non-consequential sequence variations" mean that "homologous" sequences (i.e., the sequences that have substantial sequence homology with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Use of the phrase "substantially pure" in the present specification and claims as a modifier of DNA, RNA, polypeptides or proteins means that the DNA, RNA, polypeptides or proteins so designated have been separated form their in vivo cellular environments through the efforts of human beings; as a result of this separation, the substantially pure DNAs, RNAs, polypeptides and proteins are useful in ways that the non-separated, impure DNAs, RNAs, polypeptides or proteins are not.

The invention DNA sequences were isolated employing analogous rat neuronal acetylcholine receptor subunit DNA fragments as probes in various human cDNA libraries. Due to the very low concentration of various human neuronal subunits in their native state, the frequently very localized presence of some of the human neuronal subunits in various sources of tissue, the difficulty in obtaining human neuronal (brain) tissue with which to work, as well as the hight level of care necessary to ensure the presence of intact mRNA in the human neuronal tissue being probed, a significant problem to be solved in order to achieve the objects of the present invention is identifying and obtaining suitable source(s) of DNA to probe for the desired sequences. By probing numerous human cDNA libraries, e.g., prefrontal cortex cDNA, parietal cDNA, temporal cortex cDNA, brain stem cDNA, basal ganglia cDNA, and spinal cord cDNA, various fragments of the human neuronal subunits were identified (see, for example, FIGS. 4, 5 and 6). After partial sequencing and restriction mapping of several such fragments, and comparison of such fragments to the analogous rat sequences, it was possible to identify composite DNA sequences for the human alpha2, alpha3 and beta2 subunits, as disclosed and claimed herein.

In addition to their use as coding sequences for the production of human neuronal subunits and synthetic human neuronal receptors, the invention sequences can also be used as probes for the identification of additional human neuronal sequences. This is done by probing various sources of human neuronal DNA with invention sequences, then selecting those sequences having a significant level of sequence homology with the probe employed.

Invention DNA sequences can be transformed into a variety of host cells. Eukaryotic cells such as yeast or mammalian cells are presently preferred. A variety of suitable host mammalian cells, having desirable growth and handling properties, are readily available to those of skill in the art. Especially preferred are human or rat cells for such purpose.

Similarly, a variety of suitable yeast cells are readily available to host cells for the invention sequences. Especially preferred are yeast selected from *Pichia pastoris, Saccharomyces cerevisiae, Candida tropicalis, Hansenula polymorpha*, and the like.

Alternatively, the invention DNA sequences can be translated into RNA, which can then to transfected into amphibian cells for transcription into protein. Suitable amphibian cells include Xenopus oocytes.

Cells transformed with invention DNA (or RNA) can optionally be further transformed with a reporter gene expression construct, so as to provide a ready, indirect measure of the presence of functional human neuronal receptor in the transformed cell. Such a reporter gene expression construct comprises:
 a transcriptional control element; wherein said transcription control element, in said cell, is responsive to an intracellular condition that occurs when the human neuronal nicotinic acetylcholine receptor interacts with a compound having agonist or antagonist activity with respect to said receptor, and
 a reporter gene encoding a transcription and/or translational product; wherein said product can be, directly or indirectly, readily measured; and wherein said gene is in operative association with said transcriptional control element.

Transcriptional control elements contemplated for use in this embodiment of the present invention include the c-fos promoter, the vasoactive intestinal peptide gene promoter, and the like.

Reporter genes contemplated for use in this embodiment of the present invention include the chloramphenicol transferase (CAT) gene, the gene product of which can be readily analyzed by a variety of methods known in the art. See, for example, Nielsen, et al., *Anal. Biochem.* 179, 19–23 (1989), luciferase and other enzyme detection systems such as alkaline phosphatase, β-galactosidase, and the like.

A particularly useful application of the invention sequences is the ability to prepare synthetic receptors and synthetic receptor subunits which are substantially free of contamination from other, potentially competing proteins. Thus, a cell transformed with the invention alpha2 and beta2 sequences could express a synthetic receptor consisting essentially of only the alpha2 and beta2 subunits. Such a synthetic receptor would be useful for a variety of applications, e.g., as part of an assay system free of the interferences frequently present in prior art assay systems employing non-human receptors or human tissue preparations.

Similarly, a synthetic receptor could be prepared by causing cells transformed with the invention alpha3 and beta2 sequences to express the corresponding proteins. The resulting synthetic receptor would consist essentially of only the alpha3 and beta2 subunits. Such a synthetic receptor would be useful for a variety of applications, e.g., as part of an assay system free of the interferences frequently present in prior art assay systems employing non-human receptors or human tissue preparations.

Furthermore, testing of single receptor subunits with a variety of potential agonists or antagonists would provide additional information with respect to the function and activity of the individual subunits. Such information may lead to the identification of compounds which are capable of very specific interaction with one or more of the receptor subunits. Such specificity may prove of great value in medical application.

In accordance with one aspect of the present invention, assay methods have been developed for the ready determination of the presence of functional neuronal nicotinic acetylcholine receptors. Thus, cells transformed with invention DNA or RNA sequences, or cell-lines derived from a variety of other sources can be readily screened to determine if functional receptors are produced thereby. One useful assay method is the "$^{86}$Rb ion-flux" assay, wherein the influx of $^{86}$Rb ions into test cells is measured as a function of the presence or absence of known neuronal nicotinic acetylcholine agonists or antagonists. Thus, a cell which shows no difference in the $^{86}$Rb ion flux, whether in the presence or absence of agonist or antagonist is not expressing functional neuronal receptor. This assay provides more information than is provided by a simple binding assay because it also indicates whether or not functional receptor is present.

Another useful assay method of the invention involves subjecting test cells to the following steps:
(a) analyzing said cells for the presence of alpha and beta subunits RNAs,
(b) analyzing those cells which are positive for the presence of alpha and beta subunit RNAs for their ability to bind nicotine or a nicotine agonist, relative to the nicotine binding ability of control cells known to produce neuronal nicotinic acetylcholine receptors, and
(c) determining the effect of known neuronal nicotinic acetylcholine agonists and/or antagonists on cells having the ability to bind nicotine or nicotine agonist on the influx of $^{86}$Rb ions into said cell, relative to the rate of influx of $^{86}$Rb ions into positive and/or negative control cells.

Cells can be analyzed for the presence of alpha and beta subunit RNA in a variety of ways, such as for example, by Northern hybridization, slot blot analysis, and the like.

The determination of the nicotine-binding ability of test cells can readily be determined by techniques known by those of skill in the art. For additional detail, see Example 3B below.

The $^{86}$Rb ion-flux assay is then carried out as described hereinabove.

The above-described sequence of analytical steps provides an effective way to screen large numbers of transformed cells for the expression of neuronal receptor subunit(s), the ability of such subunit(s) to bind to nicotine, nicotine agonists or nicotine antagonists, and the ability of such subunit(s) to assemble into functional receptors.

As a further step to verify the ability of test cells to produce functional receptor, mRNA from cells which are positive for the presence of alpha and beta neuronal nicotinic acetylcholine receptor subunits by the above-described assays can be injected into oocytes, which can then be assayed for the presence of functional neuronal nicotinic acetylcholine receptors. As another alternative, one can measure the electrophysiology of the positive cells (either directly or upon expression of RNA by oocytes). Positive results in each of these assays provides one with a high level of confidence that the test cells contain the coding sequences for the production of receptor, and that such receptor is indeed expressed.

In accordance with another aspect of the present invention, a method for making eukaryotic cells having neuronal nicotinic acetylcholine receptor activity is provided. Eukaryotic cells (e.g., mammalian or yeast cells) are transfected with DNA encoding at least one alpha subunit and at least one beta subunit of the neuronal nicotinic acetylcholine receptor. The resulting cells are then screened by one or more of the above-described assay methods to identify those cells which have successfully incorporated the desired DNA sequences.

The invention will now be described in greater detail by reference to the following non-limiting examples.

EXAMPLES

Plasmids comprising insert DNA encoding human α and β subunit proteins of the neuronal nicotinic acetylcholine receptor (nNAChR), isolated from various sources of human neuronal tissue, have been deposited in the ATCC. The clone names and deposit numbers are:

| Subunit | Clone Name | ATCC Accession # |
|---------|------------|------------------|
| α2 | HnAChRα2 | 68277 |
| α3 | HnAChRα3 | 68278 |
| β2 | HnAChRβ2 | 68279 |

Restriction maps of the nNAChR-encoding inserts in these clones, as compared to the corresponding rat cDNA maps, are provided in FIGS. 1, 2, and 3, respectively. The rat cDNA inserts are described in Wada et al. (1988), Science 240: 330–334 (α2); Boulter et al. (1986), Nature 319: 368–374 (α3); Boulter et al. (1987), Proc. Natl. Acad. Sci. 84: 7763–7767 (β2). EcoRI adapters (from cloning vector) are present on the ends of each insert.

Portions of the α2 and α3, and all of the β2, human neuronal NAChR subunit-encoding sequence were sequenced. The sequences of the human cDNAs were compared to the corresponding regions of the rat cDNAs, and the percent homology between the human and rat sequences are provided in FIGS. 4, 5, and 6, respectively. The nucleotide sequence homology is presented outside the parentheses, the translated amino acid sequence homology is presented in parentheses.

Additionally, actual nucleotide sequence comparisons are presented in FIGS. 7, 8 and 9. In all figures the human sequence is on top and the rat sequence is on the bottom. The nucleotide numbers for the rat sequences correspond to the actual nucleotide positions in the coding sequence. In contrast, the nucleotide numbers for the human sequences do not correspond to the coding sequences; instead, these numbers are related to the individual sequenced fragments. FIG. 7 presents the nucleotide sequence of the human α2 sequence as compared to the rat α2 sequence starting around the common BamHI site (see FIG. 4) and continuing in the 3' direction approximately 500 nucleotides. The degree of nucleotide homology in section A of FIG. 7 is 87% and in section B is 93%.

FIG. 8 presents the nucleotide sequence of the human α3 sequence starting about 50 nucleotide 3' from the 5' end of the coding sequence, and continuing in the 3' direction for about 650 nucleotides. The degree of nucleotide homology between the human and rat sequence in Section A is 86% and in Section B is 90%.

FIG. 9 presents the entire coding sequence of the cDNA encoding the human β2 subunit. It has 87% homology to the rat sequence at the nucleotide level.

Example 1

CONSTRUCTION OF EUKARYOTIC EXPRESSION VECTORS COMPRISED OF THE HUMAN NEURONAL NAChR SUBUNIT SEQUENCES

The cDNAs encoding the human neuronal NAChR subunits were inserted into the eukaryotic expression vector pSV2+Ldhfr, the construction of which is described in Example 2. Each insert was excised from its plasmid (HnAchRα2, HnAchRα3,or HnAchβ2) by digestion with EcoRI. The resultant fragments were gel purified and the ~2600 bp (α2), ~3200 bp (α3), and ~2450 bp (β2) fragments were isolated. Each insert fragment was ligated to EcoRI-digested and dephosphorylated pSV2+Ldhfr; 0.1 μg of each DNA was used. The ligation reaction was transformed into MC1061 cells and amp$^R$ colonies were selected. The desired plasmid(s) having insert in the correct orientation was (were) identified by the diagnostic fragments provided below, and named as follows:

| Subunit | Plasmid name | Diagnostic fragment |
|---|---|---|
| α2 | hα2/pSV2 | PvuII: 550, 100, 7000 bp |
| α3 | hα3/pSV2 | PvuII: 850, 7350 bp |
| β2 | hβ2/pSV2 | HindIII: 450, 7000 bp |

These plasmids have the subunit-encoding insert placed in functional association downstream of the SV40 early promoter.

Example 2

DEVELOPMENT OF MAMMALIAN CELL LINES EXPRESSING α AND β SUBTYPES OF THE RAT NEURONAL NICOTINIC ACETYLCHOLINE RECEPTOR (rNAChR)

Cell lines were developed in Ltk$^{31}$ (mouse fibroblast thymidine kinase deficient) cells by cotransfecting a plasmid comprised of an α-subunit-encoding sequence, a plasmid comprised of a β-subunit-encoding sequence, and a plasmid comprised of either the wild-type or crippled TK gene. A reporter gene expression construct can also be cotransfected into the cells to provide a transcription-based assay system. While the following examples employ eukaryotic expression vectors comprised of the rat NAChR subunit cDNA sequences, the eukaryotic expression vectors comprised of the human nNAChR cDNA sequences (Example 1) also can be used.

A. Host Cells Ltk⁻ cells are available from ATCC (accession #CCL1.3).

B. rNAChR α- and β-Expression Plasmids

The α- and β-encoding eukaryotic expression plasmids were constructed using a slightly modified pSV2dhfr parent plasmid [Subramani, et al. (1981). *Mol. Cell. Biol.* 1: 854–864] and α- and β-encoding inserts from the rat nNAChR subunit clones. The clone sources for the subunit sequences were:

| Subunit | Parent plasmid | Insert fragment |
|---|---|---|
| α2 | HYP16(9)$^a$ | ~2 Kb EcoRI |
| α3 | PCA48E(4)$^b$ | ~2 Kb HindIII-EcoRI |
| *α4.1 | HYA23-1E(1)$^c$ | ~2 Kb HindIII |
| β2 | PCx49(1)$^d$ | ~2 Kb EcoRI |

$^a$Wada et al., supra
$^b$Boulter et al., (1986), supra
$^c$Goldman et al., (1987), Cell 48:965–973
$^d$Boulter et al., (1987), supra
*This insert was placed into unmodified pSV2dhfr.

The pSV2dhfr plasmid was modified by first destroying the unique EcoRI site, then inserting a HindIII-EcoRV-EcoRI polylinker between the SV40 early promoter and the dhfr gene. To accomplish this, pSV2dhfr was cut with EcoRI, Klenow-treated, and religated. The resultant plasmid was called pSV2dhfrΔRI. Plasmid pSV2dhfrΔRI was digested with HindIII and 0.1 μg was ligated with a 100:1 molar ratio of unkinased double-stranded oligonucleotide of the following sequence:

```
AGC TTT CGA TAT CAG AAT TCG
    AA CGT ATA GTC TTA AGCTCGA
HindIII   EcoRV   EcoRI   destroyed HindIII
```

The ligation reaction was transformed into MC1061 bacterial cells, amp$^R$ colonies were selected, and plasmid was isolated. Correctly modified plasmid demonstrated a 350 bp band upon digestion with PvuII/EcoRI, and was called pSV2+Ldhfr.

To create the α2, α3, and β2 expression plasmids, 0.1 μg of pSV2+Ldhfr, or pSV2dhfr in the case of α4, and 0.1 μg of the subunit specific gel-isolated insert fragment were ligated, and the individual ligations were separately transformed into MC1061 cells. (The parent plasmids were digested with the appropriate enzyme to allow insertion of the insert noted above into the polylinker site prior to ligation.) Amp$^R$ colonies were selected and plasmid was isolated. The final plasmid names and diagnostic bands indicative of the correct orientation were:

| Subunit | Plasmid name | Diagnostic fragments |
|---|---|---|
| α2 | pSV2dhfrα2 | 1600 bp BglII |
| α3 | pSV2dhfrα3 | 600 bp PvuII; 850 bp BamHI |
| α4 | pSV2dhfrα4 | 800 bp PvuII/SstI |
| β2 | pSV2dhfrβ2 | 1800 bp PvuII |

These final plasmids have the subunit insert placed in functional association downstream of the SV40 early promoter.

C. TK+ Selection Plasmids

The TK+ plasmid cotransfected into Ltk⁻ cells along with the nNAChR subunit-expressing plasmids was either pThx59 [Zipser, et al., *Proc. Natl. Acad. Sci.* 78: 6276–6280 (1981)] which encodes the wildtype TK gene, or pThx24 (ibid.) which encodes a crippled TK gene.

D. Reporter Gene Expression Plasmid

A reporter gene expression plasmid comprised of the CAT gene regulated by the c-fos promoter, plasmid pFC4 [(Deschamps et al.), can also be cotransfected into the cells.

E. Transfection and TK+ Selection

The CaPO₄ transfection procedure used in the development of the rat nNAChR-expressing cell lines was that of Wigler, et al. (1979), *Proc. Natl. Acad. Sci.* 76: 1373–1376.

Briefly, Ltk$^{31}$ cells were grown in nonselective medium [D+10 (Dulbecco's modified Eagle's medium +10% calf serum), 100 U/ml penicillin, and 100 μg/ml streptomycin] in a 10 cm-sized dish, to 20% confluence. The three circular vector DNAs were precipitated with CaPO$_4$ and added to the cell monolayer. The vector concentrations were as follows:

| | |
|---|---|
| Thx24:α$_x$β$_2$ | 2 μg:2 μg:2 μg/ml |
| Thx59:α$_x$β$_2$ | 0.25 μg:2 μg:2 μg/ml |

The transfected cells were allowed to grow for two days in nonselective medium. After two days, the cells were passed and non-selective media was replaced with selective HAT medium (D+10+15 μg/ml hypoxanthine +1 μg/ml aminopterin +5 μg/ml thymidine), and the cells were left to grow for 10–15 days, during which time the cells were "fed" fresh selective (HAT) medium every 3–4 days. After 10–15 days, colonies appeared which indicated acceptance and expression of at least the plasmid carrying the TK gene. Colonies were transferred into separate wells of a 24-well dish and grown in selective medium for seven days, at which time individual colonies were passed into 6-well dishes and grown for another seven days in selective medium. To provide cells for freezing and subsequent molecular and functional receptor analyses, the individual clones in the 6-well dishes were passed to 100 ml dishes in selective medium for 5–7 days.

Example 3

CHARACTERIZATION OF CELL LINES EXPRESSING NAChR

The cell lines developed according to the methods of Example 2 were characterized using one or more of the methods described below.

Northern or slot blot analysis for expression of α- and β- subunit encoding messages Total RNA was isolated from 1×10$^7$ cells and 10–15 μg of RNA from each cell type were used for Northern or slot blot hybridization analysis. The inserts from the rat nNAChR-encoding plasmids were nick-translated and used as probe. In addition, the β-actin gene sequence [(Cleveland et al., Cell 20: 95–105 (1980)] was nick-translated and used as a control probe on duplicate filters to confirm the presence or absence of RNA on each blot and to provide a rough standard for use in quantitating differences in α- or β-specific mRNA levels between cell lines. The Northern and slot blot hybridization and wash conditions were as follows:

Hybridization:5×SSPE, 5×Denhardts, 50% formamide, 42° C.
Wash: 0.2×SSPE, 0.1% SDS, 65° C.

The results of these analyses showed that, while the amount of counts per minute corresponding to actin message was fairly constant among the various cells lines, the levels of α- and β-specific messages varied. Cell lines testing positive for both α- and β-specific mRNA were further tested for functional receptors.

B. Nicotine-binding assay

Cell lines which demonstrated αa- and β-specific mRNA were analyzed for their ability to bind nicotine, as compared to three control cell lines: the neuronally-derived cell lines PC12 (Boulter et al., (1986), Supra) and IMR32 (Clementi, et al. (1986); Int. J. Neurochem 47: 291–297, and the muscle-derived cell line BC3H1 (Patrick, et al., (1977); J. Biol. Chem. 252: 2143–2153). The assay was conducted as follows:

Just prior to being assayed, the transfected cells were removed from plates by scraping. PC12, BC3H1, and IMR32 (which had been starved for fresh media for seven days). Control cell lines were removed by rinsing in 37° C. assay buffer (50 mM Tris/HCl, 1 mM MgCl$_2$, 2 mM CaCl$_2$, 120 mM NaCl , 3 mM EDTA, 2 mg/ml BSA and 0.1% aprotinin at pH7.4). The cells were washed and resuspended to a concentration of 1×10$^6$/250 μl. To each plastic assay tube was added 250 μl of the cell solution, 15 nM $^3$H-nicotine, with or without 1 mM cold nicotine, and assay buffer to make a final volume of 500 μl. The assays for the transfected cell lines were incubated for 30 min at room temperature; the assays of the positive control cells were incubated for 2 min at 1° C. After the appropriate incubation time, 450 μl aliquots of assay volume were filtered through Whatman GF/C glass fiber filters which had been pretreated by incubation in 0.05% polyethyleneimine for 24 hours at 4° C. The filters were then washed twice, with 4 ml each wash, with ice cold assay buffer. After washing, the filters were dried, added to vials containing 5 ml scintillation fluid and then counted.

The IC$_{50}$ values for displacement of specifically bound $^3$H-nicotine in the three control cell lines were:

| Cell line | Nicotine concentration required to displace 50% bound nicotine (IC$_{50}$) |
|---|---|
| BC3H1 | 90 μM |
| PC12 | 40 μM |
| IMR32 | 35 μM |

C. $^{86}$Rb ion-flux assay

The ability of nicotine or nicotine agonists and antagonists to mediate the influx of $^{86}$Rb into transfected and control cells has been found to provide an indication of the presence of functional NAChRs on the cell surface. The $^{86}$Rb ion-flux assay was conducted as follows:

1. The night before the experiment, the cells were plated at 2×10$^6$ per well (i.e., 2 ml per well) in a 6-well polylysine-coated plate.
2. The culture medium was decanted and the plate was washed with 2 ml of assay buffer (50 mM hepes, 260 mM sucrose, 5.4 mM KCl, 1.8 mM CaCl$_2$, 0.8 mM MgSO$_4$, 5.5. mM glucose) at room temperature.
3. The assay buffer was decanted and 1 ml of assay buffer, containing 2 μCi/ml $^{86}$Rb, with 5 mM ouabain and agonist or antagonist in a concentration to effect a maximum response, was added.
4. The plate was incubated on ice at ice 1° C. for 4 min.
5. The buffer was decanted into a waste container and each well was washed with 3 ml of assay buffer, followed by two washes of 2 ml each.
6. The cells were lysed with 2 ×0.5 ml of 0.2% SDS per well and transferred to a scintillation vial containing 5 ml of scintillation fluid.
7. The vials are counted and the data calculated.

The positive control cells provided the following data in this assay:

| | PC12 | PC12 Maximum response | IMR32 | IMR32 Maximum response |
|---|---|---|---|---|
| | EC$_{50}$ | | EC$_{50}$ | |
| Agonist | | | | |
| nicotine | 52 μM | 2.1X$^a$ | 18 μM | 7.7X$^a$ |
| carbamylcholine | 35 μM | 3.3X$^b$ | 230 μM | 7.6X$^c$ |

-continued

|  | EC$_{50}$ | PC12 Maximum response | EC$_{50}$ | IMR32 Maximum response |
|---|---|---|---|---|
| (CCh) cytisine | 57 μM | 3.6X$^d$ | 14 μM | 10X$^e$ |
| Antagonist |  |  |  |  |
| d-tubocurarine | 0.81 μM |  | 2.5 μM |  |
| mecamylamine | 0.42 μM |  | 0.11 μM |  |
| hexamethonium | nd$^f$ |  | 22 μM |  |
| atropine | 12.5 μM |  | 43 μM |  |

$^a$200 μM nicotine
$^b$300 μM CCh
$^c$3 mM CCh
$^d$1 mM cytisine
$^e$100 μM cytisine
$^f$nd = not determined D. Nicotine-induced c-fos promoted expression of CAT In cell lines developed by cotransfection of the pFC4 c-fos-CAT plasmid along with the nNAChR subunit-encoding plasmids and the marker plasmid, the functionality of the nNAChRs can be indirectly evaluated by measuring the level of CAT activity. The CAT activity assay can be performed by any of the known methods in the art. See, for example, Nielsen et al., Anal. Biochem. 179: 19–23 (1989).

E. Xenopus oocytes assay

The functionality of the nNAChR expressed in transfected cells or encoded by the human neuronal NAChR subunit-encoding cDNAs can be evaluated in the Xenopus oocytes system. See Dascal, N. (1987), CRC Crit. Rev. Biochem. 22: 317–387, for a review of the use of Xenopus oocytes to study ion channels. RNA from transfectant cell lines or transcribed in vitro from the subunit-encoding cDNAs is injected into oocytes for translation into functional protein. The function of the expressed nNAChR can be assessed by a variety of electrophysiological techniques, including intracellular voltage recording, two-electrode voltage clamp, and patch clamp methods. The cation-conducting channel intrinsic to the NAChR opens in response to acetylcholine (ACh) or other nicotinic cholinergic agonists, permitting the flow of transmembrane current carried predominantly by sodium and potassium ions under physiological conditions. This current can be monitored directly by the voltage clamp techniques, or indirectly by intracellular voltage recording, wherein changes in membrane potential due to the net entry of cations are measured. With the intracellular voltage method, perhaps the simplest technique, a depolarization is recorded upon external application of agonist, signifying the presence of functional receptors in the oocyte membrane.

In a typical experiment to evaluate the functionality of nNAChR subunit-encoding transcripts, 15 oocytes were injected with ~5 ng of a 1:1 mixture of α and a β transcript. Other oocytes were injected with water to serve as negative controls. The oocytes were then incubated at 19° C. for 2–5 days in OR-2, an oocyte Ringer's solution of the following composition (concentration in mM): NaCl, 82.5; KCl, 2.5; Na$_2$HPO$_4$, 1; HEPES, 5CaCl$_2$, MgCl$_2$, 1pH=7.8. For electrophysiological recording, OR-2 of identical composition except at pH=7.5 was used as the basis of drug-containing solutions of the bath and agonist application pipet. During continuous intracellular voltage recording in a bath of OR-2 containing 1 μM atropine to block endogenous muscarinic acetylcholine receptor responses, a pipet containing 100 μM ACh was used to intermittently apply ACh by a local perfusion method in which the ACh is diluted by a factor of about 3–10 upon application to the oocyte.

Healthy oocytes have resting potentials in the range of −50 to −70 mV. Depolarizations due to ACh ranged from several mV to about 30 mV in different batches of oocytes injected with NAChR subunit-encoding transcripts. (Responses within a given batch of oocytes tended to be of similar magnitude.) The depolarizing responses to ACh were reversibly blocked by 100 μM d-tubocurarine, added to the bath. By contrast, water-injected oocytes did not respond at all to ACh administration under these conditions.

In a typical experiment to evaluate the nNAChR subunit-encoding RNA from transfected cell lines, total RNA was isolated from the cells and 50 ng were injected into oocytes. The oocytes were incubated and treated with acetylcholine, atropine, and d-tubocurarine as described above. Negative control oocytes were injected with RNA from a negative control cell line transfected with parent plasmid lacking a nNAChR subunit-encoding insert.

Oocytes injected with message from nNAChR-transfected cells demonstrated depolarization when treated with acetylcholine. The depolarization was blocked with d-tubocurarine. The negative control oocytes were unresponsive, as expected.

Alternatively, the functionality of nNAChRs expressed in transfected cells can be studied by standard electrophysiological techniques such as intracellular voltage recording or patch clamp, analogous to the methods described for oocytes.

Example 4

CELL LINES EXPRESSING FUNCTIONAL nNAChRs

Several cell lines were generated employing the procedures of Example 2. The resulting cell lines were then analyzed employing the assay methods described in Example 3. Results for several newly prepared cell clones are summarized below:

| Cell line | Subunits | RNA analysis | Binding | Rb flux | Oocytes |
|---|---|---|---|---|---|
| 592F | α2β2$^a$ | +/+$^b$ | +$^c$ | nd | +$^d$ |
| 243C | α3β2 | +/+ | + | nd | + |
| 244A | α4β2 | +/+ | + | nd | + |
| 244I | α4β2 | +/+ | + | nd | nd | nd = not determined
$^a$subunits are from rat NAChR
$^b$+/+ indicates that α- and β-specific mRNA was detected
$^c$+ indicates that the cell line binds agonist in a manner similar to positive control cells
$^d$+ indicates that ACh induces membrane depolarization which was blocked by d-tubocurarine.

These results show that functional nNAChRs are expressed by mammalian cells transfected with DNA encoding an α-subunit and a β-subunit of the nNAChR.

The invention has been described in detail with reference to certain particular embodiments thereof. It will be understood, however, that variations and modifications can be effected within the spirit and scope of the invention.

That which is claimed is:

1. Isolated and purified DNA consisting of the human neuronal nicotinic acetylcholine receptor alpha3 subunit-encoding portion of plasmid HnAChRα3 (ATCC accession No. 68278), and degenerate variants thereof.

2. Recombinant cells containing DNA according to claim 1.

3. Recombinant cells according to claim 2, wherein said cells further contain at least one DNA encoding a beta2 subunit of an human neuronal nicotinic acetylcholine receptor.

4. Recombinant cells according to claim 3, wherein said cells are eukaryotic cells.

5. Recombinant cells according to claim 4, that are yeast or mammalian cells.

6. mRNA transcribed from the alpha3-encoding DNA of claim 1.

7. Recombinant cells containing mRNA according to claim 6, wherein said cells are bacterial cells, mammalian cells, yeast cells or amphibian oöcytes.

8. Recombinant cells according to claim 7, wherein said cells further contain mRNA encoding a beta2 subunit of an human neuronal nicotinic acetylcholine receptor.

9. Recombinant cells according to claim 8 that are amphibian cells.

10. Isolated and purified DNA consisting of the human neuronal nicotinic acetylcholine receptor beta2 subunit-encoding portion of plasmid HnAChRβ2 (ATCC accession No. 68279), and degenerate variants thereof.

11. Recombinant cells containing DNA according to claim 10.

12. Recombinant cells according to claim 11, wherein said cells are further transformed with at least one DNA encoding an alpha subunit of an human neuronal nicotinic acetylcholine receptor.

13. Recombinant cells according to claim 12, wherein said cells are eukaryotic cells.

14. Recombinant cells according to claim 13, that are yeast or mammalian cells.

15. mRNA transcribed from the beta2-encoding DNA of claim 10.

16. Recombinant cells containing mRNA according to claim 15.

17. Recombinant cells according to claim 16, wherein said cells further contain mRNA encoding an alpha subunit of an human neuronal nicotinic acetylcholine receptor.

18. Recombinant cells according to claim 17 that are amphibian cells.

* * * * *

UNITED STATES PATENT AND TRADEMARK OFFICE

CERTIFICATE OF CORRECTION

PATENT NO.: 5,369,028

DATED: November 29, 1994

INVENTOR(S): Harpold, Michael M., et. al.

It is certified that error appears in the above-identified patent and that said Letters Patent is hereby corrected as shown below:

ON THE TITLE PAGE:

On the title page of the patent, section [75], entitled Inventors, should read "Michael M. Harpold; Steven B. Ellis, both of San Diego, Calif."

Signed and Sealed this

Twenty-sixth Day of August, 1997

Attest:

BRUCE LEHMAN

Attesting Officer

Commissioner of Patents and Trademarks